United States Patent [19]

Nudelman et al.

[11] Patent Number: 5,418,129
[45] Date of Patent: May 23, 1995

[54] BLOOD TREATMENT METHOD

[75] Inventors: Edward Nudelman; Anil Singhal; Henrik Clausen, all of Seattle; Sen-itiroh Hakomori, Mercer Island, all of Wash.; Kazuo Muroi; Toshio Suda, both of Minamikawachi, Japan; Hisao Nojiri, Seattle, Wash.

[73] Assignees: The Biomembrane Institute, Seattle, Wash.; Jichi Medical School, Tochigi, Japan

[21] Appl. No.: 803,065

[22] Filed: Dec. 6, 1991

Related U.S. Application Data

[63] Continuation-in-part of Ser. No. 787,778, Nov. 6, 1991, Pat. No. 5,240,833, which is a continuation of Ser. No. 387,683, Jul. 31, 1989, abandoned, which is a continuation of Ser. No. 302,890, Jan. 30, 1989, abandoned.

[51] Int. Cl.$^6$ .............. A01N 1/02; C12P 21/08; C07K 15/28; A61K 39/395
[52] U.S. Cl. ............ 435/2; 435/70.21; 435/240.27; 530/388.23; 530/388.25; 424/140.1
[58] Field of Search ........ 435/2, 240.27, 70.21; 530/388.8, 388.23, 388.25; 424/140.1

[56] References Cited

U.S. PATENT DOCUMENTS 4,904,596 2/1990 Hakomori .............. 435/240.27

OTHER PUBLICATIONS

Ritz J. et al, The Lancet, 2:60–63, Jul. 10, 1982.

Primary Examiner—Christina Y. Chan
Assistant Examiner—Susan A. Loring
Attorney, Agent, or Firm—Sughrue, Mion, Zinn, Macpeak & Seas

[57] ABSTRACT

A method of producing monoclonal antibodies that bind to tumor-associated gangliosides, the method comprising: (1) immunizing a host with tumor cells; (2) boosting the host with a suspension comprising a mixture of tumor cell membrane and at least one purified lactonized tumor-associated ganglioside; (3) boosting the host with an immunogen comprising a lactone of a tumor associated ganglioside adsorbed on or incorporated into a carrier; (4) fusing immunized cells from the host with myeloma cells to form hybridoma cells; (5) selecting hybridoma cells that produce antibody that binds to the ganglioside of step (3); (6) culturing the selected hybridoma cells; and (7) recovering the antibody.

4 Claims, 5 Drawing Sheets

1 2 3 4 5 6 7 8 9 10 11
NKH1

FIG. 3B

1 2 3 4 5 6 7 8 9 10 11
NKH2

FIG. 3C 1 2 3 4 5 6 7 8 9 10 11
NKH3

FIG. 3D 1 2 3 4 5 6 7 8 9 10 11
anti-Le$^a$

FIG. 4

BLOOD TREATMENT METHOD

Portions of the subject matter disclosed herein were supported in part by grants from the National Cancer Institute, Department of Health & Human Services.

This is a continuation-in-part application of U.S. Ser. No. 07/787,778 filed 6 Nov. 1991, U.S. Pat. No. 5,240,833, which is a continuation of application U.S. Ser. No. 07/387,683 filed 31 Jul. 1989, now abandoned, which is a continuation application of U.S. Ser. No. 07/302,890 filed 30 Jan. 1989, now abandoned.

FIELD OF THE INVENTION

The present invention relates to an improved method for producing monoclonal antibodies to tumor-associated gangliosides, to the hybridomas and monoclonal antibodies produced therefrom and to the use of said antibodies. More particularly, the present invention relates to new methods for preparing monoclonal antibodies directed to tumor-associated gangliosides which use in the immunization steps a booster of purified ganglioside lactones. The present invention also relates to the novel hybridomas produced by the improved method and to the novel monoclonal antibodies produced by the hybridomas. The monoclonal antibodies are useful, for example, in the detection and treatment of tumors containing gangliosides.

BACKGROUND OF THE INVENTION

Cells are surrounded by plasma membranes. Plasma membranes contain components called glycosphingolipids inserted therein which aid in the formation of the characteristic surface structure of cells. Each type of cell is characterized by a specific profile of glycosphingolipid components, including those components known as gangliosides, located in its plasma membrane. Gangliosides contain a particular type of acidic carbohydrate known as sialic acid. Further, many specific types of cells, including tumor cells, are characterized by the presence of a particular type of ganglioside located in their plasma membranes.

In recent years, a number of monoclonal antibodies have been established after immunization with human tumor cells or tissues. The monoclonal antibodies were selected by positive reactivity with tumor cells and negative reactivity with normal cells or tissues. Many monoclonal antibodies selected for preferential reactivity with melanomas, neuroblastomas and adenocarcinomas have been identified are directed to gangliosides.

Some of the anti-ganglioside antibodies with specific isotypes (particularly $IgG_3$ and $IgG_{2a}$) and which show strong reactivity with gangliosides suppress tumor growth in vivo. For example, melanomas of some patients regressed following large dose administration of a specific anti-$GD_3$ ganglioside antibody (Houghton, A. N. et al., *Proc. Natl. Acad. Sci. USA*, 82:1242–1246 (1985)).

Further, it was demonstrated recently that $GM_2$ adsorbed on BCG bacteria showed a detectable immune response. Thus, it was asserted that $GM_2$ could be a useful vaccine for human melanomas (Livingston, P.O. et al., *Proc. Natl. Acad. Sci. USA*, 84:2911–2915 (1987)).

Hence, gangliosides are important antigens and immunogens of tumor tissues and cells (Hakomori, S., *Ann. Rev. Immunol.*, 2:103–126 (1984); Hakomori, S., In *Handbook of Lipid Research*, Volume 3, *Sphingolipid Biochemistry*, Kanfer, J. N. et al., Eds., Plenum, New York, pages 1–165 (1983); and Hakomori, S., *Sci. Amer.*, 254:44–53 (1986)).

However, although gangliosides are important cell type-specific markers, gangliosides are poor immunogens for eliciting humoral or cellular immune responses.

A small portion of gangliosides are present in tumor cells and tissues in the form of a lactone thereof. For example, less than 0.1% of the particular ganglioside, designated $GM_3$, present in melanoma cells was identified as a lactone thereof.

Ganglioside lactones are defined as the inner ester between the carboxyl group of the sialic acid and the primary or secondary hydroxyl group of the sugar residues within the same molecule.

While galactoside lactones have been detected and are believed to occur naturally as plasma membrane components, the quantity thereof is extremely low and thus the natural occurrence thereof is disputed (Nores, G. A. et al., *J. Immunol.*, 139:3171–3176 (1987) and Riboni, L., *J. Biol. Chem.*, 261:8514–8519 (1986)).

Despite the question about the natural occurrence of said lactones, it was demonstrated that ganglioside lactones are strong immunogens which can cause a much greater immune response than native gangliosides (Nores, G. A. et al., *J. Immunol.*, 139:3171–3176 (1987)). Further, Nores et al., supra, found that the antibodies produced using ganglioside lactones as immunogens often are of the $IgG_3$ isotype.

In the present invention, it was found that the use of tumor cells and tumor cell membranes followed by a booster with purified ganglioside lactones in the immunization step of producing hybridomas provides new hybridomas that produce monoclonal antibodies (mAb's) directed to a variety of tumor-associated gangliosides, including human cancer-associated fucogangliosides. Further, while some of the new antibodies show similar binding specificity to known antibodies, the isotypes thereof are different. Therefore the pharmacodynamic activities thereof also are expected to be different. Further, many of the new antibodies have unique cross-reactivity.

Monoclonal antibodies directed to lacto-series type 2 chain structures such as i, $Le^x$ $Le^y$ and, sialosyl-$Le^x$ are known to react with a large number of common human cancers derived from tissues of lung, breast, stomach, colon, liver, pancreas and other endodermal epithelial sources. For example, Hoff et al., *Canc. RES.*, 49:6883–6888 (1989) and Inafusa et al., *Clin. Exp. Metas.*, 9:245–257 (1991) found high expression of sialyl $Le^x$ in metastatic tumors.

Some of the tumor-associated carbohydrate antigens (TACA's) also are expressed in normal mature myelocytes and monocytes, as well as in leukemic leukocytes. However, it is unknown whether those TACA's are expressed in hematopoietic cells or progenitors and in leukemic leukocytes. Data on expression of those TACA's in hematopoietic progenitor cells is desirable since mAb's directed to type 2 chain-based structures could serve as useful clinical reagents for targeting leukemic leukocytes as well as solid tumors if the antigens are not expressed or are expressed at lower levels in normal or progenitor cells.

SUMMARY OF THE INVENTION

Accordingly, an object of the present invention is to provide an improved method for producing antibodies to tumor-associated gangliosides, and especially tumor-associated fucogangliosides.

It is also an object of the present invention to provide novel hybridomas that produce monoclonal antibodies to particular tumor-associated antigens.

It is further an object of the present invention to provide novel monoclonal antibodies to particular tumor-associated antigens.

Another object of the present invention is to provide a passive immunization method for treating tumors containing gangliosides or malignancies of the circulatory system wherein the affected cells contain gangliosides.

Still another object of the present invention is to provide a method for detecting tumors containing gangliosides.

A sixth object of the present invention is to provide a method of selective isolation or removal of antigen-bearing cells from a mixed population of cells.

And yet another object of the present invention is to provide a method of treating inflammation.

Those and other objects of the present invention, which will be apparent from the detailed description of the invention provided hereinafter, have been met by the following embodiments.

In one embodiment, the present invention relates to a method of producing monoclonal antibodies that bind to tumor-associated gangliosides, the method comprising:
 (1) immunizing a host with tumor cells;
 (2) boosting said host with a suspension comprising a mixture of tumor cell membrane and at least one purified lactonized tumor-associated ganglioside;
 (3) boosting said host with an immunogen comprising a lactone of a tumor associated ganglioside adsorbed on or incorporated into a carrier;
 (4) fusing immunized cells from said host with myeloma cells to form hybridoma cells;
 (5) selecting hybridoma cells that produce antibody that binds to said ganglioside of step (3);
 (6) culturing said selected hybridoma cells; and
 (7) recovering said antibody.

The present invention also provides a hybridoma cell line that produces a monoclonal antibody having the following identifying characteristics:
 (1) Isotype is IgM; and
 (2) Binds to:
  (a) sialyl $Le^x$, and
  (b) sialyl difucosyl Lex;

A hybridoma cell line that secretes a monoclonal antibody having the following identifying characteristics:
 (1) Isotype is $IgG_1$; and
 (2) Binds to sialyl 2→3 $Le^a$; A hybridoma cell line that secretes a monoclonal antibody having the following identifying characteristics:
 (1) Isotype is IgM; and
 (2) Binds to:
  (a) sialyl 2→3 $Le^a$;
  (b) $Le^a$;
  (c) pentaosylceramide and hexaosylceramide carrying the $Le^a$ epitope;
  (d) $Le^a/Le^x$ hybrid; and
  (e) bivalent $Le^a$ on lactoisooctaosylceramide;

A hybridoma cell line that produces a monoclonal antibody having the following identifying characteristics:
 (1) Isotype is $IgG_1$; and
 (2) Binds to:
  (a) sialyl 2→3 $Le^a$; and
  (b) sialyl 2→3 type 1 chain paragloboside, when tested with auxiliary lipids or by TLC immunostaining with a plastic-coated plate; and A hybridoma cell line that produces a monoclonal antibody having the following identifying characteristics:
 (1) Isotype is $IgG_3$; and
 (2) Binds to:
  (a) sialyl difucosyl $Le^x$; and
  (b) sialyl monofucosyl extended $Le^x$.

In a further embodiment, the present invention provides the monoclonal antibodies produced by the above-identified hybridomas.

In an even further embodiment, the present invention provides a passive immunization method for treatment of tumors containing gangliosides comprising administering to a subject:
 a pharmaceutically effect amount of an antibody produced by a method comprising:
  (1) immunizing a host with tumor cells;
  (2) boosting said host with a suspension comprising a mixture of tumor cell membrane and at least one purified lactonized tumor-associated ganglioside;
  (3) boosting said host with an immunogen comprising a lactone of a tumor associated ganglioside adsorbed on or incorporated into a carrier;
  (4) fusing immunized cells from said host with myeloma cells to form hybridoma cells;
  (5) selecting hybridoma cells that produce antibody that binds to said ganglioside of step (3);
  (6) culturing said selected hybridoma cells; and
  (7) recovering said antibody.

In an even further embodiment, the present invention provides a method for detecting tumors containing gangliosides comprising:
 (A) contacting a test sample with an antibody produced by a method comprising:
  (1) immunizing a host with tumor cells;
  (2) boosting said host with a suspension comprising a mixture of tumor cell membrane and at least one purified lactonized tumor-associated ganglioside;
  (3) boosting said host with an immunogen comprising a lactone of a tumor associated ganglioside adsorbed on or incorporated into a carrier;
  (4) fusing immunized cells from said host with myeloma cells to form hybridoma cells;
  (5) selecting hybridoma cells that produce antibody that binds to said ganglioside of step (3);
  (6) culturing said selected hybridoma cells; and
  (7) recovering said antibody; and
 (B) Assaying for specific binding of said antibody to antigen in said test sample.

In a further embodiment, the present invention provides a method of treating malignancies of the circulatory system comprising administering to a subject in need of treatment:
 a pharmaceutically effective amount of an antibody produced by a method comprising:
  (1) immunizing a host with tumor cells;
  (2) boosting said host with a suspension comprising a mixture of tumor cell membrane and at least one purified lactonized tumor-associated ganglioside;
  (3) boosting said host with an immunogen comprising a lactone of a tumor associated ganglioside;

(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

In yet another embodiment, the instant invention provides a method of treating blood for transplantation comprising exposing blood to:

a therapeutically effective amount of an antibody produced by a method comprising:
(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

In yet a further embodiment, the instant invention provides a method for separating blood cells comprising exposing blood to:

a therapeutically effective amount of an antibody produced by a method comprising:
(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

In another embodiment, the instant invention provides a method of treating inflammation comprising administering to a subject in need of treatment:

a pharmaceutically effective amount of an antibody produced by a method comprising:
(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

BRIEF DESCRIPTION OF THE FIGURES

FIG. 1 is a graph showing the results of a radioimmunoassay using monoclonal antibody SNH3 according to the present invention. The ordinate represents the activity of protein A binding to primary and secondary antibody, in counts per minute. The abscissa represents the antigen dilution wherein the first well (denoted as 1) contained 100 ng antigen, the second well (denoted as 2) contained 50 ng antigen etc. The open circles represent sialyl difucosyl Le$^x$ (structure 2, Table I; VI$^3$NeuAcV-$^3$FucIII$^3$FucNLc$_6$) isolated from tumors. The open triangles represent the same antigen but synthesized enzymatically from sialyl 2→3 norhexaosylceramide. The closed, upside down triangles represent sialyl Le$^x$ hexasaccharide ceramide isolated from tumors (structure 1, Table I; IV$^3$NeuAcIII$^3$FucnLc$_4$).

The open, upside down triangle represent sialyl 2→3 norhexaosylceramide. The closed circles represent GM$_3$, 2→3 sialylparagloboside (SPG) (IV$^3$NeuAcnLc$_4$, 2→6 SPG (VI$^6$NeuAcnLc$_4$), sialyl 2→3 Le$^a$ (structure 3, Table I; IV$^2$NeuAcIII$^4$FucLc$_4$), and sialyl 2→6 norhexaosylceramide (VI$^6$NeuAcnLc$_6$).

FIGS. 2A–2E depict graphs showing the reactivity of antibodies NKH1 (FIG. 2A), NKH2 (FIG. 2B), NKH3 (FIG. 2C), NKH4 (FIG. 2D) and CF4C4 (a known anti-Le$^a$ antibody; FIG. 2E) by solid-phase radioimmunoassay. The ordinate represents the activity of protein A binding to secondary antibody which reacts with primary antibody bound to the antigen. The abscissa represents the antigen dilution as described for FIG. 1 above. The open triangles represent sialyl 2→3 Le$^a$ purified from tumors (structure 3, Table I; IV$^3$-NeuAcIII$^4$FucLc$_4$). The open, upside down triangles represent the same antigen but isolated from meconium (also contains disialyl Le$^a$). The closed squares represent sialylparagloboside (SPG) type 1 chain. The closed triangles represent Le$^a$ (structure 5, Table I; III$^4$-FucLc$_4$). The closed, upside down triangles represent an Le$^a$/Le$^x$ hybrid (structure 7, Table I). The closed circles represent bivalent Le$^a$ on lactoisooctaosylceramide (iso-Le$^a$) (structure 8, Table I). The open squares represent synthetic sialyl 2→3 paragloboside.

FIGS. 3A–3D show immunostaining patterns of various glycolipid samples with antibodies NKH1 (FIG. 3A), NKH2 (FIG. 3B), NKH3 (FIG. 3C) and an anti-Le$^a$ antibody (FIG. 3D). Lane 1: monosialoganglioside fraction of meconium; lane 2: monosialoganglioside fraction of meconium treated with sodium methoxide (to determine possible presence of gangliosides containing an O-acetyl group); lane 3: upper neutral glycolipids of O erythrocytes; lane 4: monosialoganglioside fraction from human colonic cancer cell line Colo 205; lane 5: Le$^a$-active ceramide pentasaccharide (III$^4$FucLc$_4$Cer; structure 5, Table I); lane 6: sialyl 2→3 paragloboside type 1 chain isolated from meconium (structure 4, Table I); lane 7: sialyl 2→3 paragloboside type 1 chain synthesized from CMP-sialic acid and Lc$_4$Cer (type 1 chain paragloboside) (structure 4, Table I); lane 8: sialyl 2→3 Le$^a$ (IV$^3$NeuAcIII$^4$FucLc$_4$Cer; structure 3, Table I ); lane 9: Le$^a$ on Le$^x$ (IV$^3$Gal$\beta$1→3[Fuc$\alpha$1→4]GlcNAc-III$^3$FucnLc$_4$Cer; structure 7, Table I); and lane 10: Le$^a$ on branched lactoisooctaosylceramide (V$^3$FucIV$^6$-Gal$\beta$1→3-[Fuc$\alpha$1→3]GlcNAcnLc$_6$Cer; structure 8, Table I).

FIG. 4 depicts the binding specificity of SNH4. Antigens were diluted serially starting from 100 ng/well (1) as in FIG. 1. Open circles represent sialyl difucosyl Le$^x$; closed circles represent sialyl monofucosyl extended Le$^x$ (IV$^3$NeuAcIII$^3$FucNLc$_6$); open triangles represent sialyl Le$^x$; and closed triangles represent sialyl paragloboside.

DETAILED DESCRIPTION OF THE INVENTION

According to the present invention there is provided a novel method of producing monoclonal antibodies directed to tumor-associated gangliosides. An important aspect of the method is that the immunization of the host includes a booster step using a lactone of a tumor associated ganglioside.

The method comprises:

(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside adsorbed on or incorporated into a carrier;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

The particular tumor cells and tumor cell membrane used in steps (1) and (2), respectively, of the method are not limited particularly and any of those used conventionally in the production of hybridomas that produce antibodies to tumor cell antigens can be used (Fukushi et al., *J. Biol. Chem.*, 259:4672–4680 (1984) and *J. Biol. Chem.*, 259:10511–10517 (1984)).

Specific examples of tumor cell antigens include colonic cancer cells (e.g., SW948 and Colo 205) and human lung carcinoma cells (e.g., PC9).

Immunization with the tumor cells is conducted according to conventional methods.

The membrane fraction used in step (2) is prepared in a conventional manner (Fukushi et al., *J. Biol. chem.*, 59:4572–4680 (1984) and *J. Biol. Chem.*, 259:10511–10517 (1984)).

A mixture of a tumor cell membrane and at least one purified lactonized tumor-associated ganglioside is used for immunization in step (2). The mixture can be prepared by adding purified lactonized tumor-associated ganglioside to a membrane fraction and incubating at pH 6.0–6.5 (at that pH, lactones are stable). Alternatively the mixture can be prepared by treating the mixture by known methods to lactonize the tumor cell membrane gangliosides and the purified ganglioside.

For example, the membrane fraction is prepared, suspended in 5% acetic acid, mixed with purified gangliosides and then lyophilized. That procedure induces lactonization and enrichment of membrane gangliosides.

The lyophilized material is suspended in PBS and injected intravenously, according to well known methods.

The particular tumor-associated ganglioside employed in steps (2) and (3) of the present invention is not critical hereto. Examples of such tumor-associated gangliosides include GD3 found in melanomas (Pukel, C. S. et al., *J. Exp. Med.*, 155:1133–1147 (1982) and Nudelman, E. et al., *J. Biol. Chem.*, 257:12752–12756 (1982)); GD2 found in melanomas and neuroectodermal tumors such as neuroblastomas (Cahan, L. et al., *Proc. Natl. Acad. Sci. USA*, 79:7629–7633 (1982)); sialyl Le$^a$ found in gastrointestinal and pancreatic cancers (Magnani, J. L. et al., *J. Biol. Chem.*, 257:14365–14369 (1982)); sialyl Le$^x$ found in colorectal, gastrointestinal and lung adenocarcinomas (Fukushima, K. et al., *Cancer Res.*, 44:5279–5285 (1984)); sialyl difucosyl Le$^x$ found in colorectal, gastrointestinal and lung adenocarcinomas (Fukushi, Y. et al., *J. Biol. Chem.*, 259:10511–10517 (1984)); GM3 found in melanomas (Taniguchi, M., *Gann*, 75:418–426 (1984); Hirabayashi, Y. et al., *J. Biol. Chem.*, 260:13328–13333 (1985); and Nores, G. et al., *J. Immunol.*, 139:3171–3176 (1987)); 6C ganglioside found in colorectal carcinomas (Hakomori, S. et al., *Biochem. Biophys. Res. Commun.*, 113:791–798 (1983)); G2 ganglioside found in myelogenous leukemia cells (Fukuda, Y. et al., *J. Biol. Chem.*, 260:1060–1082 (1985)); disialosyl Le$^a$ found in colorectal cancers (Nudelman, E. et al., *J. Biol. Chem.*, 261:5487–5495 (1986)); monosialyl type 1 chain found in colorectal carcinomas and teratocarcinomas (Nilsson, O. et al., *FEBS Letters*, 282:398–402 (1985) and Fukuda, M. N. et al., *J. Biol. Chem.*, 261:5145–5153 (1986)); disialosyl type 1 chain found in colorectal cancers (Fukushi, Y. et al., *Biochem.*, 25:2859–2866 (1986)); and fucosyl GM$_1$ found in small cell lung carcinomas (Nilsson, O et al., *Glycoconjugate J.*, 143–149 (1984)).

Lactones of the gangliosides for use in step (3) of the method can be prepared by known methods (Nores, G. A. et al., *J. Immunol.*, 139:3171–3176 (1987)).

For example, the lactones can be prepared by dissolving any ganglioside in glacial acetic acid and allowing the solution to stand for at least 48 hours, followed by lyophilization of the acetic acid. Formation of the ganglioside lactones can be monitored by thin layer chromatography using high performance thin layer chromatography plates obtained from J. T. Baker Chemical Co. (Phillipsburg, N.J.) and chloroform:methanol:water (50:40:10 (v/v/v)) containing 0.05% (w/v) CaCl$_2$ as a solvent since ganglioside lactones show a distinctively higher mobility than native gangliosides on thin layer chromatography. The above solvent composition is not critical and any well known solvent which can separate gangliosides from the lactones thereof can be employed, for example, as described in Nores, G. A. et al., *J. Immunol.*, 139:3171–3176 (1987).

Alternatively, and more efficiently, ganglioside lactones can be prepared by dissolving any ganglioside in chloroform:methanol:12N HCl (10:35:4.5 (v/v/v)) and allowing the solution to stand for about one day. The resulting solution then is chromatographed using DEAE-Sephadex in chloroform:methanol:water (0.1:1:1 (v/v/v)). Two main components and several minor components, the structures of the latter remain to be elucidated, are resolvable in that system. The resulting ganglioside lactones can be purified by HPLC on Iatrobeads 6RS8010 in isopropanol:hexane:water (55:25:20 (v/v/v)) with gradient elution being carried out as described by Watanabe, K. et al., *J. Lipid Res.*, 22:1020–1024 (1981). The structure of the purified ganglioside lactones can be verified by direct probe fast atom bombardment mass spectrometry as described in Riboni, L., *J. Biol. Chem.*, 261:8514–8519 (1986).

Ganglioside lactones also can be prepared by treatment with carbodiimide (Sonnino, S. et al., *Glycoconjugate J.*, 2:343–354 (1985)).

The purified lactonized ganglioside is administered intravenously to the host along with a suitable carrier.

The particular carrier to be used along with the lactone of the tumor-associated ganglioside is not critical to the present invention. Examples of such acceptable carriers include acid-treated *Salmonella minnesotae*, reconstituted viral membranes such as Newcastle's disease virus membranes and any reconstituted cell membranes incubated with octylglucose followed by dialysis.

The particular host immunized for eventual production of hybridomas is not critical to the present invention. Examples of suitable hosts include mice, rabbits, rats and goats.

As used herein "immunized cells" refers to the sensitized spleen cells of the immunized host, e.g., those of mice such as BALB/c mice.

The particular myeloma cell employed in the present invention is not critical thereto and can be any well known myeloma cell useful for preparing hybridomas of mouse, rat, rabbit, goat and human origin. Examples of such myeloma cells include HAT-sensitive mouse myeloma cells such as NS1 cells and SP2 cells.

The amount of tumor cells, membrane/ganglioside mixture and lactone of the tumor-associated ganglioside to be administered in the present invention will vary depending upon the age, weight, sex and species of the animal being immunized and can be determined readily by the skilled artisan. By way of example, one suitable immunogenic effective amount of the lactone is about 2.0 to 5.0 μg, absorbed on about 20 to 100 μg of carrier per one injection.

Immunizing the animals, e.g., mice, with the ganglioside lactones of the present invention, isolating the immunized cells, fusing the immunized cells with, e.g., mouse myeloma cells, and culturing the resulting fused cells under conditions which allow for growth of hybridomas, are all conducted by methods well known and readily determined in the art (Young, W. W. et al., *J. Exp. Med.*, 150:1008–1019 (1979) and Fukushi, Y. et al., *J. Biol. Chem.*, 259:4681–4685 (1984)).

The resulting hybridomas then are screened so as to isolate those which produce monoclonal antibodies having binding specificity to the ganglioside used to prepare the lactone in step (3), in, for example, a solid-phase radioimmunoassay using ganglioside-coated wells and assaying using a second antibody (rabbit anti-mouse IgM+IgG (Miles Biochemical, Elkhart, Ind.)) and $^{125}$I-labeled Protein A.

Monoclonal antibodies secreted by hybridomas thus isolated according to the method of the present invention can be produced in quantity by growing large batches of hybridoma cell cultures and purifying the antibody from the supernatant or by injecting mice with the hybridoma line to stimulate the production of ascites fluid. Both methods are known well in the art.

The hybridomas isolated according to the present invention can be grown in large batches in suspension culture, or more conveniently in a fiberglass container in which cells are packed and grown in high density, wherein antibodies diffuse into the culture medium.

Methods of producing monoclonal antibody in quantity according to the present invention are described, for example, in Young et al. (supra).

The monoclonal antibodies can be purified by known methods, for example, affinity separation using protein A, high pressure liquid chromatography on a reverse phase alkylated silica gel or with a synthetic polystyrene gel filtration column.

According to the above described method, new hybridomas that produce new monoclonal antibodies directed to a variety of tumor-associated gangliosides, including human cancer-associated fucogangliosides, can be made. The new antibodies have isotypes different from known antibodies showing similar binding specificity and many of the new antibodies have unique cross-reactivity. Further, the method differs over the previous method for immunizing with fucogangliosides in that unexpectedly, monoclonal antibodies having isotypes other than $G_3$ are obtained. The antibodies have, for example, the M and $G_1$ isotypes.

For example, antibody SNH4 was obtained by immunizing mice with membrane preparations of PC-9 cells expressing sialyl Le$^x$ which were later boosted with sialyl difucosyl Le$^x$ lactone. SNH4 is an IgG$_3$ antibody.

Six preferred monoclonal antibodies that have been isolated according to the above method are SNH3, SNH4, NKH1, NKH2, NKH3 and NKH4. The hybridomas that produce the monoclonal antibodies, designated hybridoma SNH3, SNH4, NKH1, NKH2, NKH3 and NKH4, respectively, were deposited with the American Type Culture Collection, Rockville, Maryland, and have ATCC Deposit Nos. HB 9941, HB 10518, HB 9942, HB 9943, HB 9944 and HB 9945, respectively.

Monoclonal antibody SNH3 according to the present invention is produced by hybridoma SNH3 and has the following identifying characteristics:

(1) Isotype is IgM;
(2) Binds primarily to:
   (a) sialyl Le$^x$ and
   (b) sialyl difucosyl Le$^x$; and
(3) Binds weakly, particularly on TLC immunostaining with pretreating by plastic coating material, to:
   (a) 2→3 sialylnorhexasoyl ceramide (VI$^3$-NeuAcnLc$_6$), and
   (b) extended Le$^x$ (VI$^3$NeuAcIII$^3$FucnLc$_6$).

The reactivity is distinct from that of many similar known antibodies, including FH6 and CSLEX. Monoclonal antibody SNH4 according to the present invention is produced by hybridoma SNH4 and has the following identifying characteristics:

(1) Isotype is IgG$_3$; and
(2) Binds to:
   (a) sialyl difucosyl Le$_x$; and
   (b) sialyl monofucosyl extended Le$^x$.

Monoclonal antibody NKH1 according to the present invention is produced by hybridoma NKH1 and has the following identifying characteristics:

(1) Isotype is IgG$_1$; and
(2) Binds to sialyl 2→3 Le$^x$.

The reactivity is similar to that of known monoclonal antibodies N-19-9 and CSLEA. However, the isotype of monoclonal antibody NKH1 is different from that of N-19-9 and CSLEA and thus its pharmacodynamic activity is expected to be different from that of N-19-9 and CSLEA. Monoclonal antibody NKH2 according to the present invention is produced by hybridoma NKH2 and has the following identifying characteristics:

(1) Isotype is IgM; and
(2) Binds to:
   (a) sialyl 2→3 Le$^a$,
   (b) Le$^a$,
   (c) pentaosylceramide and hexaosylceramide carrying the Le$^a$ epitope,
   (d) Le$^a$/Le$^x$ hybrid and
   (e) bivalent Le$^a$ on lactoisooctaosylceramide.

Monoclonal antibody NKH2 is unique in its cross-reactivity with Le$^a$-containing structures. Monoclonal antibodies NKH3 and NKH4 according to the present invention are produced by hybridomas NKH3 and NKH4, respectively, and have the following identifying characteristics:

(1) Isotype is IgG$_1$; and
(2) Bind to:
   (a) sialyl 2→3 Le$^a$, and (b) sialyl 2→3 type 1 chain paragloboside when tested with auxiliary lipids or by TLC immunostaining with a plastic-coated plate.

Monoclonal antibodies NKH3 and NKH4 are similar to monoclonal antibody CA50 in apparent reactivity, but the isotypes thereof are different. Thus the pharmacodynamic activities of monoclonal antibodies NKH3 and NKH4 are expected to be different from the pharmacodynamic activity of monoclonal antibody CA50. Further, the reactivity of monoclonal antibodies NKH3 and NKH4 with sialyl 2→3 Le$^a$ is quite clear regardless of experimental conditions, whereas cross reactivity with sialyl type 1 chain paragloboside is unclear, unless the reactivity is tested with auxiliary lipids or by TLC immunostaining with a plastic coated plate as is described in more detail in the working examples.

A summary of the isotypes of monoclonal antibodies SNH3, NKH1, NKH2, NKH3 and NKH4 according to the present invention and a detailed listing of the binding specificities of those monoclonal antibodies is set forth in Table I on the following page.

TABLE I

Reactivity of tumor-associated gangliosides with monoclonal antibodies: NH3, NKH1, NKH2, NKH3 and NKH4

| Structure | NH3 (IgM) | NKH1 (IgG1) | NKH2 (IgM) | NKH3 (IgG1) | NKH4 (IgG1) |
|---|---|---|---|---|---|
| 1. NeuAcα2→3Galβ1→4GlcNAcβ1→3Galβ1→4Glcβ1→1Cer<br>　　　　　　　　　　　3↑<br>　　　　　　　　　　Fucα1 | + | − | − | − | − |
| 2. NeuAcα2→3Galβ1→4GlcNAcβ1→3Galβ1→4GlcNAcβ1→3Galβ1→4Glcβ1→1Cer<br>　　　　　　　　　　　3↑　　　　　　　　　　　3↑<br>　　　　　　　　　Fucα1　　　　　　　　　　Fucα1 | + | − | − | − | − |
| 3. NeuAcα2→3Galβ1→3GlcNAcβ1→3Galβ1→4Glcβ1→1Cer<br>　　　　　　　　　　　4↑<br>　　　　　　　　　Fucα1 | − | + | + | + | + |
| 4. NeuAcα2→3Galβ1→3GlcNAcβ1→3Galβ1→4Glcβ1→1Cer | − | − | + | + | + |
| 5. Galβ1→3GlcNAcβ1→3Galβ1→4Glcβ1→1Cer<br>　　　　　4↑<br>　　Fucα1 | − | − | + | + | − |
| 6. Galβ1→4GlcNAcβ1→3Galβ1→4Glcβ1→1Cer<br>　　　　　3↑<br>　　Fucα1 | − | − | − | − | − |
| 7. Galβ1→3GlcNAcβ1→3Galβ1→4GlcNAcβ1→3Galβ1→4Glcβ1→1Cer<br>　　　　　4↑　　　　　　　　　　3↑<br>　　Fucα1　　　　　　　　　　Fucα1 | − | − | + | − | − |

TABLE I-continued

Reactivity of tumor-associated gangliosides with monoclonal antibodies: NH3, NKH1, NKH2, NKH3 and NKH4

| Structure | NH3 (IgM) | NKH1 (IgG₁) | NKH2 (IgM) | NKH3 (IgG₁) | NKH4 (IgG₁) |
|---|---|---|---|---|---|
| 8.  | − | − | + | − | − |

Lacto-series type 2 antigens based on the backbone structure Gal$\beta$1→4GlcNAc$\beta$1→3Gal$\beta$1→R with sialosyl or fucosyl substitutions (e g., Le$^x$ Le$^y$, sialosyl-Le$^x$, dimeric Le$^x$ etc.) are a major type of TACA in various human cancers derived from endodermal epithelial cells. Many mAb's directed to those epitopes react with various human cancer tissues, certain stages of embryonic gastrointestinal mucosa or embryonic lung buds. While the expression of those antigens in normal adult tissues is highly restricted, the mAb's to those TACA's react with mature granulocytes (or neutrophilic granulocytes) and monocytes. For that reason, clinical application of anti-type 2 chain mAb's in cancer therapy has been hampered.

As disclosed herein, type 2 chain-derived antigens are expressed in normal mature granulocytes and in leukemic blasts from patients with acute myeloblastic leukemia (AML) or acute unclassified leukemia (AUL). For example, one anti-sialosyl-Le$^x$ mAb, SNH3, is reactive with essentially all populations of (>95%) leukemic blast cells from all AML and AUL patients tested. Significantly, the anti-type 2 chain mAb's did not react with hematopoietic progenitor cells which were stained by anti-CD34 mAb, as evidenced by two-color flow cytometry. Hematopoietic colonies derived from progenitor cells (CFU-GM and CFU-E) were observed after treatment of normal bone marrow cells with mAb SNH3 plus complement. Mature granulocytes, monocytes and leukemic myeloblasts all were stained with anti-type 2 chain mAb's such as SNH3.

The present invention also provides a passive immunization method for treatment of tumors containing gangliosides. The method comprises administering to a subject:

A pharmaceutically effective amount of an antibody produced by a method comprising:
(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside adsorbed on or incorporated into a carrier;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody.

The details of producing the antibody have been described above.

A pharmaceutically acceptable diluent can be employed in the immunization method of the present invention. The particular pharmaceutically acceptable diluent employed is not critical thereto. Examples of such diluents include physiological saline, Ringer's solution, vitamin cocktail and amino acid vitamin cocktail.

For administration of antibody to produce an anti-tumor effect in vivo, no carrier should be used. Purified antibodies are given intravenously without carrier material.

The pharmaceutically effective amount of the antibodies of the present invention to be administered will vary depending upon the age, weight, sex and species of the animal to be treated. Generally, the pharmaceutically effective amount is about 1.0 to 5.0 $\mu$g/100 g body weight of animal per one injection. Generally, from 5 to 10 injections of the antibodies are employed but the present invention is not limited thereto.

The particular antibody which will be administered will depend upon the particular ganglioside present in the tumor which is to be treated. Information as to the particular ganglioside present in the tumor can be obtained by a serum assay or biopsy assay for the various gangliosides. As used herein, "treatment" means both prevention of tumor formation and treatment of existing tumors.

The present invention also provides a method for detecting tumors containing gangliosides comprising:
(A) contacting a test sample with an antibody produced by a method comprising:
(1) immunizing a host with tumor cells;
(2) boosting said host with a suspension comprising a mixture of tumor cell membrane and at least one purified lactonized tumor-associated ganglioside;
(3) boosting said host with a lactone of a tumor associated ganglioside adsorbed on or incorporated into a carrier;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody; and
(B) assaying for specific binding of said antibody to antigen in said test sample.

In the method for detecting tumors containing gangliosides of the present invention, "test sample" means, for example, tissue biopsies, serum, ascites fluid and spinal fluid.

The method of producing the antibody has been described in detail above.

Detection can occur either in vitro or in vivo. In vitro detection can be carried out using any of the well known in vitro immunologic assays, such as those described by Young, W. W. et al., *J. Exp. Med.*, 50:1008–1019 (1979) and Kannagi, R. et al., *Cancer Res.*, 43:4997–5005 (1983). Further, in vivo detection can be carried out using any of the well known in vivo immunologic assays, such as those described in Burcheil, J. et al., *Int. J. Cancer*, 34:763–768 (1984); Epenetos, A. A. et al., *Lancet*, 2:999–1004 (1982); Chatal, J.-F. et al., *J. Nuclear Med.*, 25:307–314 (1984); Munz et al., *J. Nuclear Med.*, 27:1739–1745 (1986); and Kennan, A. N. et al., *J. Nuclear Med.*, 26:531–537 (1985).

In another embodiment, the mAb's of the instant invention can be used to purge myelogenous leukemic cells and leukemic blasts from a mixed cell population, e.g., during bone marrow transplantation. Autologous bone marrow transplantation, in particular, can be achieved by purging leukemic cells, for example, using a combination of antibodies and complement, cytotoxic drug conjugates and/or microsphere magnetic beads coated with anti-type 2 chain mAb's.

As used herein, "blood" means, for example, whole blood, bone marrow aspirates, blood products or blood components such as packed cells, purified cell populations and the like, the cellular and acellular elements normally suspended in the fluid state and any artificial fluid medium, which may or may not contain cellular or acellular elements, that can be used as a blood substitute.

As used herein, "circulatory system" represents that art-recognized term to include the blood vascular system, the lymph vascular system and the immune system, along with all of the cellular and acellular elements contained therein and associated therewith and the organs associated therewith such as the heart, spleen, GALT (a assemblage of lymphoid elements in the gut), thymus, lymph nodes and the like.

In yet another embodiment, the instant mAb's can be used to treat common solid tumors which generally are characterized by high expression of type 2 chain TACA's. Since hematopoietic progenitor cells do not express the antigens, the mAb's can be used to target tumor cells and their metastatic deposits, through, for example, either drug delivery or activation of cytotoxic cells and complement.

In another embodiment, anti-sialosyl-Le$^x$ mAb's are used to treat inflammatory processes, which often are characterized by the recruitment and adhesion of leukocytes at the site of inflammation by LECCAM's or selectins. Two LECCAM's, ELAM-1 and GMP-140 express the carbohydrate (CHO) epitope recognized as sialosyl-Le$^x$. Thus, application of anti-sialosyl-Le$^x$ mAb's can block the initial step of inflammation. Because the epitope is not expressed in hematopoietic progenitor cells, the treatment presumably would not have serious side effects.

EXAMPLES

The following examples are provided for illustrative purposes only and are in no way intended to limit the scope of the present invention.

EXAMPLE 1

Production of SNH3, an IgM antibody defining sialyl Le$^x$ (structure 1, Table I)

SNH3 antibody was established after immunization of mice with tumor cells and lactonized sialyl difucosyl Le$^x$ as follows. A million SW948 colonic cancer cells were injected intraperitoneally into BALB/c mice twice at weekly intervals (weeks 1 and 2). Next, $10^6$ human lung carcinoma PC9 cells were injected intraperitoneally at weeks 3 and 4. Finally, at week 5, lactonized sialyl difucosyl Le$^x$ adsorbed on *Salmonella minnesotae* was injected intravenously. Lactonization of sialyl difucosyl Le$^x$ ganglioside and adsorption on *S. minnesotae* followed by immunization were performed as previously described (Nores, G. A. et al., *J. Immunol.*, 139:3171–3176 (1987)). Lactonization of sialyl difucosyl Le$^x$ was performed in glacial acetic acid (Nores, G. A. et al., *J. Immunol.*, 139:3171-3176 (1987)) or treated with carbodiimide as described recently (Sonnino, S. et al., *Glycoconjugate* 2:343-354 (1985)).

In the case of sialyl difucosyl Le$^x$ lactone antigen, 5 μg of the antigen was adsorbed on 40 μg of *S. minnesotae* suspended in 200 μl of phosphate buffered saline (PBS) and injected intravenously. Three days after the lactone injection, spleen cells were harvested and fused with mouse myeloma SP2 or NS1. Clones were screened by positive reactivity with the sialyl difucosyl Le$^x$ antigen (structure 2, Table I) and specificity of the antibody secreted by established hybridoma SNH3 was examined by TLC immunostaining and solid-phase radioimmunoassay according to known methods.

Figure 1:
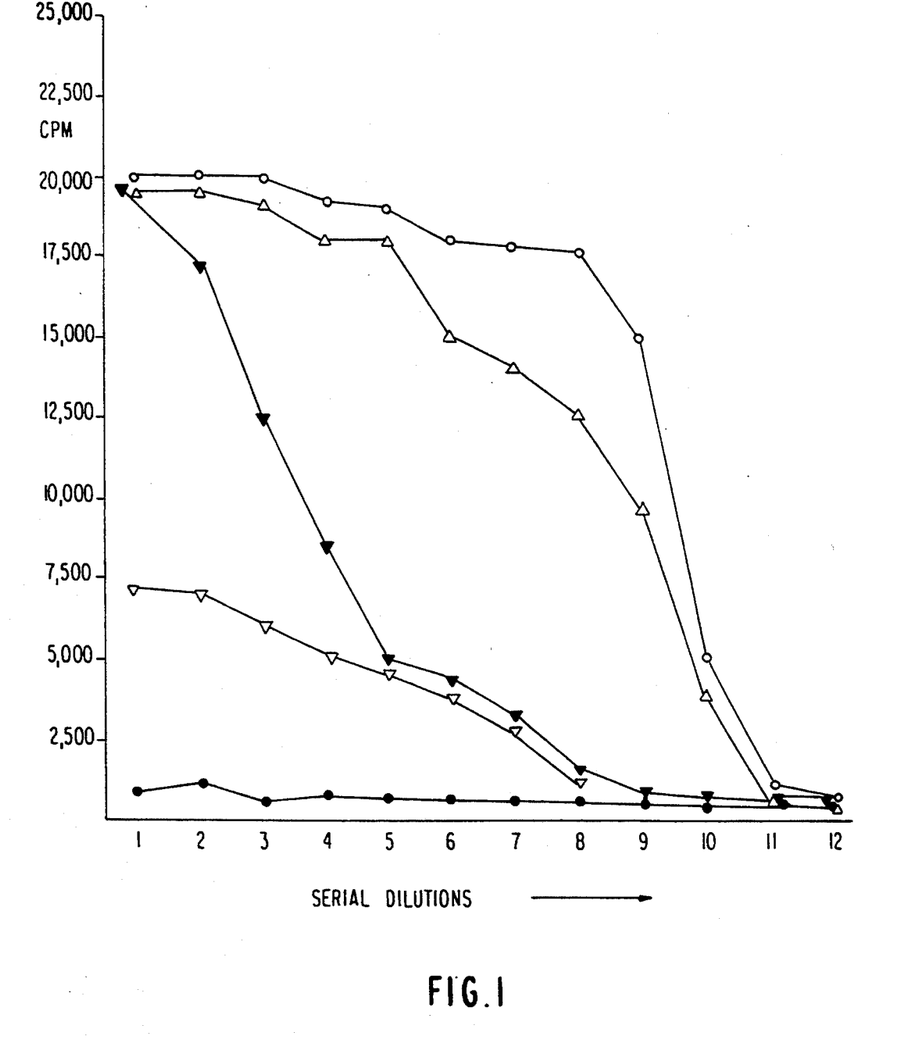

Reactivity of the antibody SNH3 is shown in FIG. 1. Solid-phase radioimmunoassay was performed as described previously (Kannagi, R. et al., *Cancer Res.*, 43:4997–5005 (1983)). The ordinate indicates the activity of protein A binding to primary and secondary antibody. The abscissa indicates antigen dilution, i.e., the first well (denoted as 1) contained 100 ng antigen, second well (denoted as 2) contained 50 ng antigen, etc. Open circles, sialyl difucosyl Le$^x$ (structure 2, Table I) isolated from tumors. Open triangles, the same antigen synthesized enzymatically from sialyl 2→3 norhexaosylceramide. Closed, upside down triangles, sialyl Le$^x$ hexasaccharide ceramide isolated from tumors (structure 1, Table I). Open, upsidedown triangles, sialyl 2→3 norhexaosylceramide. Closed circles, GM3, 2→3 sialylparagloboside (SPG) (IV$^3$NeuAcnLc4), 2→6 SPG (IV$^6$NeuAcnLc4), sialyl 2→3 Le$^a$ (structure 3, Table I), sialyl 2→6 norhexaosylceramide (VI$^6$NeuAcnLc6).

The data in FIG. 1 shows that SNH3 antibody reacts preferentially with long-chain sialyl difucosyl Le$^x$ but also reacts reasonably well with short-chain sialyl Le$^x$ (i.e., sialyl Le$^x$ hexasaccharide ceramide). It also is weakly reactive with sialyl 2→3 lactonorhexaosylceramide (VI$^3$NeuAcnLc6), and sialyl 2→3 lactonorhexaosylceramide having a fucosyl residue at the internal GlcNAc (VI$^3$NeuAcIII$^3$FucnLc6). SNH3 is non-reactive with other related structures. The reactivity is distinctive from known reactivities of similar antibodies, i.e., it is different from that of FH6 (which does not react with short-chain sialyl Le$^x$ (IV$^3$NeuAcIII$^3$FucnLc4)) and CSLEX (which does not react with internally fucosylated sialyl 2→3 norhexaosyl or with sialyl 2→3 norhexaosyl structures). The antibody is particularly useful as a diagnostic reagent for serum assay of a large variety of human carcinomas.

EXAMPLE 2

Production of NKH1, 2, 3 and 4 defining sialyl 2→3 Le$^a$ (structure 3, Table I) and sialyl 2-3 type 1 chain (structure 4, Table I)

The isotype and specificity of each antibody are as follows:

| | |
|---|---|
| NKH1 | IgG$_1$; reacts specifically with sialyl 2→3 Le$^a$. |
| NKH2 | IgM; reacts primarily with sialyl 2→3 Le$^a$ but cross-reacts with Le$^a$. |
| NKH3 | IgG$_1$; reacts with both sialyl 2→3 Le$^a$ and SPG type 1 chain (similar to specificity of CA50). |
| NKH4 | IgG$_1$; reacts with both sialyl 2→3 Le$^a$ and SPG type 1 chain (very similar to NKH3; subtle difference can be seen in degree of cross-reactivity between the two ganglioside species). |

The procedures for preparation of the hybridomas were as follows:

a) BALB/c mice were immunized with $5 \times 10^6$ Colo 205 whole cells intraperitoneally 3 times at intervals of 1 week.

b) Membrane fraction of Colo 205 was prepared by known methods, suspended in 5% acetic acid, mixed with 3-5 μg purified gangliosides (sialyl 2→3 Le$^a$ and SPG type 1 chain) and lyophilized. That procedure induces lactonization and enrichment of membrane gangliosides. The material from lyophilization was suspended in PBS and injected intravenously at week 4.

c) about 3-5 μg of purified lactonized ganglioside (sialyl 2→3 Le$^a$), prepared as described in Example 1, coated on 40 μg *S. minnesotae* in 200 μl saline by the method described in Example 1 were injected intravenously at week 5.

d) Spleen was harvested 3 days after the 5th injection and the splenocytes were fused with SP2 cells. Hybridomas were selected by specific reactivity with purified gangliosides sialyl 2→3 Le$^a$ and SPG type 1 chain as described in Example 1.

All hybridomas (NKH1, −2, −3 and −4) were prepared by the same procedure.

The reactivity of the NKH series antibodies by solid-phase radioimmunoassay is shown in FIGS. 2A–2E and the TLC immunostaining data is shown in FIGS. 3A–3D.

The procedure used for solid-phase radioimmunoassay was as described previously (Kannagi, R. et al., *Cancer Res.*, 43:4997–5005 (1983)). The antibody CF4C4 is a known anti-Le$^a$ antibody and was used to confirm that the Le$^a$ activity of various samples used for assay NKH1, 2, 3 and 4 to detect cross reactivity. The glycolipids having Le$^a$ determinants, such as structures 5, 7 and 8 in Table I, were positive with CF4C4 and structure 3 was negative with CF4C4 but positive with NKH2.

The meaning of the symbols in FIGS. 2A–2E are as follows. Open triangles, sialyl 2→3 Le$^a$ purified from tumors (structure 3, Table I). Open, upside down triangles, the same antigen isolated from meconium (also contains disialyl Le$^a$). Closed squares, SPG type 1 chain. Closed triangles, Le$^a$ antigen (structure 5; Table I). Closed, upside down triangles, an Le$^a$/Le$^x$ hybrid (structure 7, Table I). Closed circles, iso-Le$^a$ (structure 8, Table I). Open squares, synthetic sialyl 2→3 paragloboside.

Figures 3A, 3B:
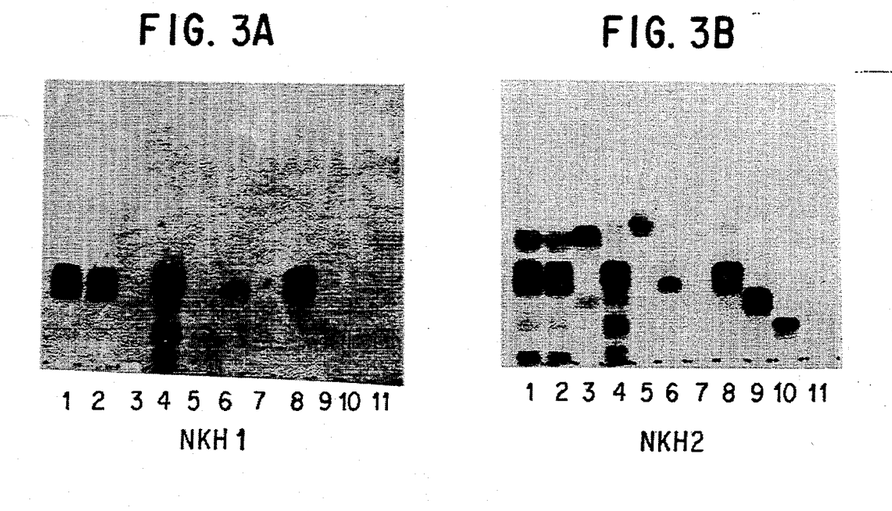

For the immunostaining patterns of various glycolipid samples with the respective antibodies shown in FIGS. 3A–3D, glycolipids on each lane were developed in chloroform-methanol-water containing 0.01% CaCl$_2$ (55:30:10 v/v/v). The HPTLC plates were stained by a modified procedure of Magnani et al. (Magnani, J. L. et al., *Anal. Biochem.*, 109:399–402 (1980)). Lane 1: monosialoganglioside fraction of meconium; lane 2: monosialoganglioside fraction of meconium treated with sodium methoxide (in order to determine possible presence of gangliosides containing O-acetyl group); lane 3: upper neutral glycolipids of O erythrocytes; lane 4: monosialoganglioside fraction from human colonic cancer cell line Colo 205; lane 5: Le$^a$-active ceramide pentasaccharide (III$^4$FucLc$_4$Cer; structure 5, Table I); lane 6: sialyl 2→3 paragloboside (PG) type 1 chain isolated from meconium (structure 4, Table I); lane 7: sialyl 2→3 paragloboside (SPG) type 1 chain synthesized from CMP-sialic acid and Lc$_4$Cer (type 1 chain paragloboside) (structure 4, Table I); lane 8: sialyl 2→3 Le$^a$ IV$^3$NeuAcIII$^4$FucLc4Cer; structure 3, Table I); lane 9: Le$^a$ on Le$^x$ determinant (IV$^3$Gal$\beta$1→3-[Fuc$\alpha$1→4]GlcNAc-III$^3$FucnLc$_4$Cer; structure 7, Table I); and lane 10: Le$^a$ on branched lactoisooctaosylceramide (V$^3$FucIV$^6$Gal$\beta$1→3-[Fuc$\alpha$1→3]GlcNAcnLc$_6$Cer; structure 8, Table I). The spot seen in lane 6 of FIG. 3B is due to contamination of 2→3 sialyl Le$^a$ and is not an indication of specificity.

Figure 2A:
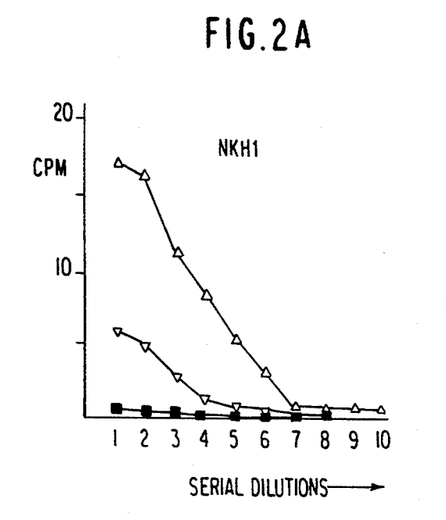

The data in FIGS. 2A–2E and in FIGS. 3A–3D show the following:

(1) NKH1 is highly specific to sialyl 2→3 Le$^a$ and does not cross-react with 2→3 sialyl paragloboside (SPG) type 1 chain or paragloboside (PG) type 1 chain. The reactivity is similar to that of previously described antibodies such as N-19-9 (Magnani, J. L. et al., *J. Biol. Chem.*, 257:14365–14369 (1982)) and CSLEA (Chia, D. et al., *Cancer Res.*, 45:435–437 (1985)). However, the isotype of NKH1 is different from that of N-19-9 and CSLEA.

Figure 2B:
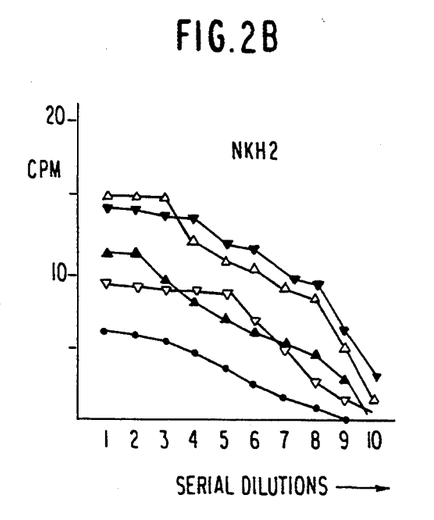

(2) Antibody NKH2 is characterized by the way it reacts with both Le$^a$ and sialyl 2→3 Le$^a$. A weak reactivity also was demonstrated with PG type 1 chain. Such reactivity is novel; i.e., an antibody with such specificity has not been described previously.

Figure 2C:
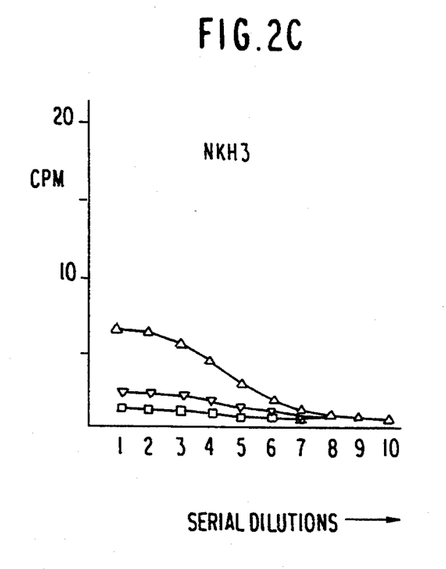
Figure 2D:
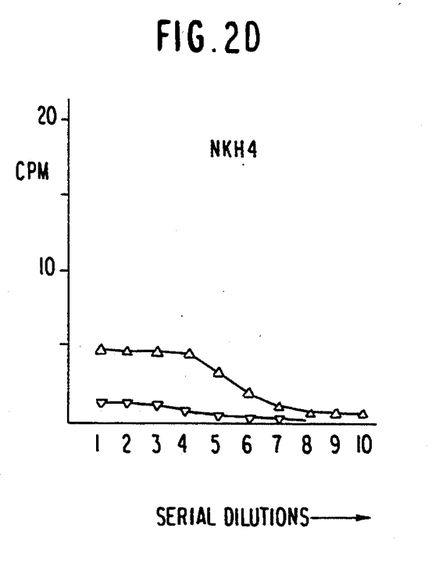
Figure 2E:
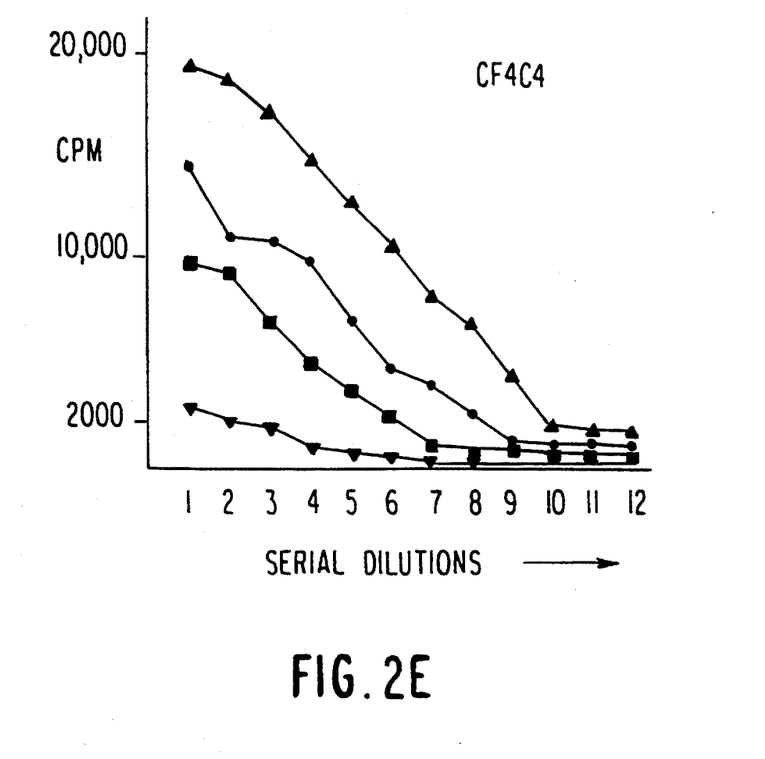
Figure 3C:
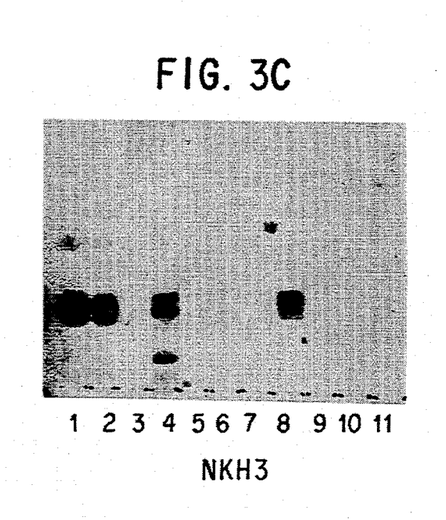
Figure 3D:
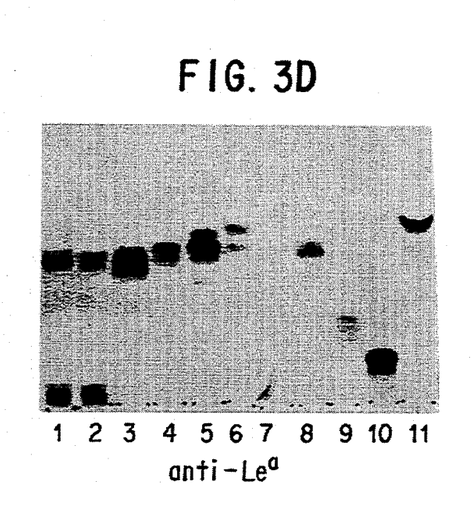
Figure 4:
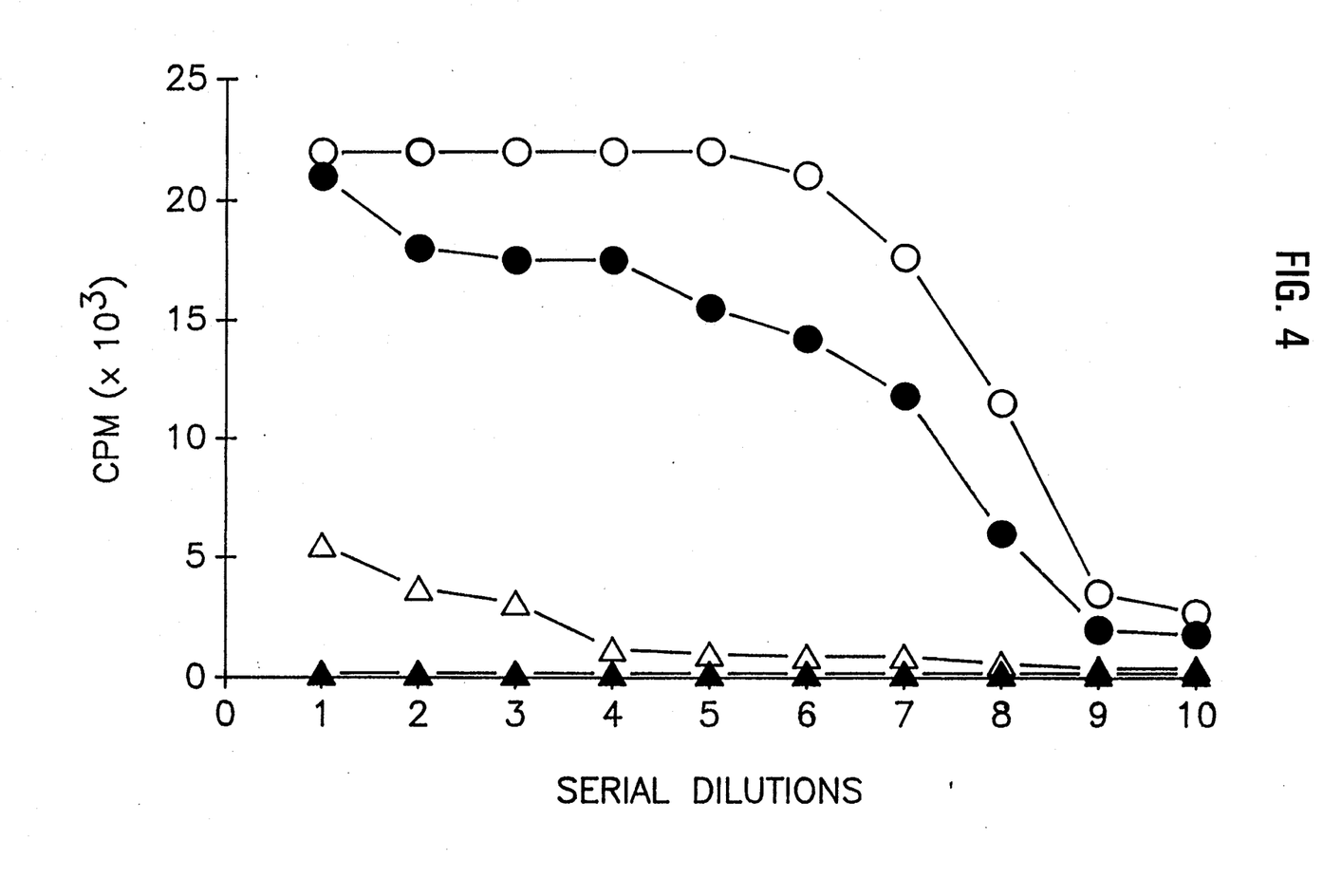

(3) NKH3 and NKH4 react with both sialyl 2→3 Le$^a$ and sialyl 2→3 type 1 chain on TLC immunoblotting, although on solid-phase radioimmunoassay the reactivity with sialyl 2→3 Le$^a$ and SPG type 1 chain is weak.

To further test detailed specificity, type 1 chain analogues were synthesized enzymatically, as well as hybrid glycolipids having the structure on Le$^x$ (structure 7, Table I) and bivalent Le$^x$ on lactoisooctaosylceramide (structure 8, Table I).

The hybrid structure Le$^a$ on Le$^x$ as well as bivalent Le$^a$ were reactive only with NKH2 antibody.

EXAMPLE 3

Antibody Specificity

Cells and cell lines

Normal peripheral blood samples were obtained from healthy volunteers. Heparinized samples were incubated with mAb's directed to carbohydrate antigens for 30 minutes at 4° C. After being hemolyzed and washed, samples were divided into three fractions (neutrophil-rich, monocyte-rich, and lymphocyte-rich) by fluorocytogram in a flow cytometer (Spectrum III, Becton-Dickinson). Platelet-rich and erythrocyte-rich fractions were obtained by centrifuging peripheral blood samples.

Peripheral blood and bone marrow blood samples were obtained after informed consent from patients with acute myeloblastic leukemia (AML), acute lymphoblastic leukemia (ALL), acute unclassified leukemia (AUL), adult T cell leukemia (ATL) or leukemia non-Hodgkin lymphoma. Diagnosis of leukemia was according to the morphologic classification of acute leukemias by the French-American-British Cooperative Group (Bennett, J. et al., *Ann. Int. Med.*, 103:620 (1985)). Samples were diluted with phosphate buffered saline (PBS), layered over Ficoll-Metrizoate (Lymphoprep; Nyegaard, Oslo, Norway) and centrifuged at 400×g for 30 minutes at room temperature. Interphase mononuclear cells obtained from the patients contained over 90% leukemic blasts. Cells were washed twice with PBS, passed through a stainless steel mesh and washed once with staining medium (2% fetal calf serum (FCS) and 0.1% sodium azide in PBS).

Human erythroleukemia cell line K562, promyelocytic leukemia cell line HL60, monocytic leukemia cell line THP1, T-lymphoblastic leukemia cell line MOLT4, pre-B lymphoblastic leukemia cell lines NALM18 and KM3 and B-lymphoblastic leukemia cell line BALL1 were obtained from American Type Culture Collection or donated by Dr. Jun Minowada (Fujisaki Cell Center, Hayashibara Biochemical Laboratory, Japan). All leukemia cell lines were cultured in RPMI-1640 medium supplemented with 10% FCS in a 5% CO$_2$ incubator at 37° C.

Immunophenotyping

Normal peripheral blood cells or leukemic blasts were incubated with human gamma-globulin (Cohn Fraction II) to block cell Fc receptors. Cells then were stained with mAb's directed to carbohydrate (CHO) antigens or with a panel of well-characterized mouse mAb's (Mol [CD11b], MY7 [CD13], MY9 [CD33], HPCA1 [CD34], OKBcalla [CD10], B4 [CD19], B1 [CD20], Leu1 [CD5], Leu9 [CD7] and I2 [HLA-DR]) for 30 minutes at 4° C. Subsequently, FITC-conjugated anti-mouse polyclonal immunoglobulin was added to anti-CHOmAb-treated or HPCA1-treated cells. Other mAb's were used in a direct immunofluorescence test. All anti-CHOmAb's were used as the hybridoma culture supernatant. In preliminary experiments, addition of 50 μl supernatant (approximate Ig concentration in supernatant was 10 μg/ml) was sufficient for reactivity with leukemia cell lines. Therefore that volume was used in subsequent experiments. Fluorescence was analyzed using a Spectrum III flow cytometer. Reactivity was defined as positive when more than 20% of cells were stained by a mAb.

Dual staining procedure

A standard procedure was used. Briefly, mononuclear cells from normal adult bone marrow were pelleted for staining with mAb's. Cells were incubated with HPCA1 (mouse $IgG_1$, anti-CD34 mAb, Becton-Dickinson Immunocytometry Systems, Mountain View, Calif.) and one of the anti-CHO mAb's for 30 minutes on ice, washed twice and subsequently treated with FITC-conjugated rat anti-mouse $IgG_1$ mAb (Zymed Laboratories, San Francisco, Calif.) and phycoerythrin-conjugated rat anti-mouse $IgG_3$ or IgM mAb. In other experiments, mononuclear cells also were stained with HPCA1 and MY9 (mouse $IgG_{2a}$, anti-CD33 mAb, Coulter Immunology, Hialeah, FL) or with HPCA1 and I2 (mouse $IgG_{2a}$, anti-HLA-DR mAb, Coulter). The cells then were treated with FITC-conjugated rat anti-mouse $IgG_1$ mAb and phycoerythrin-conjugated rat anti-mouse $IgG_2$ mAb. The cells were suspended in staining medium containing 7-aminoactinomycin D. Unstained cells or cells stained only with second mAb were included as negative controls.

Stained cells were analyzed on FACStar$^{plus}$ (Becton-Dickinson). Multiparameter data were collected and analyzed using the FACS-DESK program (version 1.2) run on a Digital Micro VAX-II GPX. Fluorescence intensity of individual cells was measured as relative fluorescence units. Data from more than 50,000 bone marrow mononuclear cells were obtained.

Cytotoxicity assay

HL60 cells and patient leukemic blasts were treated with anti-CHO mAb and baby rabbit complement (Pel-Freeze Clinical Systems, Brown Deer, Wis.). Fifty microliters of supernatant of each hybridoma were added to a cell pellet ($3 \times 10^5$ cells). The pellet was mixed adequately and incubated for 15 minutes at 4° C. Fifty microliters of complement then were added to the mixture to a final concentration of 1:2, 1:4 or 1:6 v/v. The mixture was incubated for 15 to 75 minutes at 37° C. and the reaction was stopped immediately by immersion in an ice water bath. Untreated cells were incubated with RPMI-1640 medium supplemented with 5% FCS. Cell cytotoxicity was measured by trypan blue dye exclusion.

Leukemic colony assay

Fifty microliters of mAb SNH3 (approximately 10 μl Ig per ml) were added to a cell pellet ($1 \times 10^3$ HL60 cells or $5 \times 10^4$ patient leukemic blasts). The pellet was mixed and incubated for 15 minutes at 4° C. Fifty microliters of complement then were added to the mixture to a final concentration of 1:2, 1:4, or 1:6 v/v. The mixture was incubated for 45 minutes at 37° C. Untreated cells were incubated with Iscove's medium containing 5% FCS then put on ice and washed twice with the same medium. (HL60 cells were plated in 35 mm plastic dishes (Falcon, Oxnard, Calif.) in quadruplicate. The culture medium consisted of 1.2% methylcellulose in Iscove's medium with 30% FCS (Flow Laboratories, North Ryde, NSW, Australia), 1% deionized bovine serum albumin (BSA) (Sigma Chemical Co., St. Louis, Mo.) and 1% glutamine. Patient leukemic cells were plated in 35 mm plastic dishes in quadruplicate. The culture medium consisted of 1.2% methylcellulose in Iscove's medium with 30% FCS, 1% BSA, 1% phytohemagglutinin-activated-lymphocyte conditioned medium (PHA-LCM), 1% L-glutamine and $5 \times 10^{-5}$ mol/L 2-mercaptoethanol.) Cells were incubated at 37° C. in a humidified 5% $CO_2$ atmosphere and scored after 10 days for colonies (>20 cells) using an inverted microscope.

Hematopoietic progenitor cell assay

Mononuclear cells ($5 \times 10^4$) from normal adult bone marrow were treated with 50 μl of SNH3 for 15 minutes at 4° C. Fifty microliters of complement then were added to the mixture to a final concentration of 1:2, 1:4 or 1:6 v/v. The mixture was incubated for 45 minutes at 37° C. Untreated cells were incubated with Iscove's medium containing 5% FCS, then put on ice and washed twice with the same medium. The cells were plated in 35 mm plastic dishes (Falcon) in quadruplicate. The culture medium consisted of 1.2% methylcellulose in Iscove's containing 30% FCS, 1% BSA, 1% PHA-LCM, 2 U/ml erythropoietin, 1% L-glutamine and $5 \times 10^{-5}$ mol/L 2-mercaptoethanol. Cells were incubated at 37° C. in a humidified 5% $CO_2$ atmosphere and scored after 14 days for colonies (>40 cells) using an inverted microscope.

SNH3 (anti-sialosyl-Le$^x$) reacted with monocytes and neutrophils. SNH3 also reacted with HL60, K562, as well as THP1 cells. Because SNH3 reacted with monocytes and neutrophils, it is expected to react with immature and mature myeloid lineage cells.

SNH3 reacted strongly with leukemic blasts from all AML patients and from two AUL patients.

SNH3 showed strong cytotoxicity of HL60 cells and to leukemic monoblasts from one AML patient. Cytotoxicity of SNH3 was complement-dependent. After treatment with SNH3 and complement, HL60 viability decreased to less than 5%. Similarly, after treatment with SNH3 and complement, viability of leukemic monoblasts decreased to less than 15%. Optimal concentration of complement producing cytotoxicity against HL60 cells and leukemic monoblasts was 1:4 v/v and optimal incubation time for cytotoxicity was 45 minutes.

SNH3 markedly suppressed leukemia colony-forming units (LCFU) of HL60 cells and of leukemic monoblasts. In clonal cell culture, SNH3 showed >98% inhibition of colony formation in both HL60 cells and leukemic monoblasts.

EXAMPLE 4

Reactivity of anti-CHO mAb's with CD34-positive cells

Since SNH3 reacted with AML leukemic blasts having the progenitor cell antigen CD34, the reactivity of the mAb with CD34-positive normal hematopoietic progenitor cells was examined. CD34-positive cells were not detected in the SNH3-positive cell fractions. As positive controls, mononuclear bone marrow cells were stained dually with CD34 and CD33, or with CD34 and anti-HLA-DRmAb. CD34-positive cells were detected in the CD33- and anti-HLA-DR mAb-positive cell fractions. The findings indicate that SNH3 does not react with normal hematopoietic progenitor cells.

To confirm that result, the effect of SNH3 on growth of normal hematopoietic progenitor cells was examined. The colony-forming efficiency of hematopoietic cells, especially CFU-GM, was inhibited incompletely by treatment of bone marrow mononuclear cells with SNH3 and complement. The efficiency of BFU-E was inhibited slightly by the same treatment. Those findings indicate that SNH3 reacts with committed progenitor cells (myeloblasts) but not with uncommitted pluripotent progenitor cells.

EXAMPLE 5

Leukocytes trafficking and recruitment to the sites of inflammation are mediated through the activation of blood vessel endothelial cells. Two of the adhesion proteins, ELAM-1 and CD62 (GMP140) expressed on activated endothelial cells were found to bind leukocytes through a receptor, sialyl Le$^x$, expressed on leukocytes. Phillips et al., *Science*, 250:1130–1132 (1990) and Polley et al., *Proc. Natl. Acad. Sci. USA*, 88:6224–6228 (1991).

Monoclonal antibodies SNH3 and SNH4 block that binding and thus block the transfer of leukocytes to the sites of inflammation.

Accordingly, diseases and injuries resulting in inflammation and tissue damage by leukocyte infiltration are treatable by antibodies such as SNH4 (only antibody with that specificity and with the IgG isotype).

Furthermore, the antibodies can block cancer metastasis by blocking the transfer of highly metastatic cancer cells expressing sialyl Le$^x$ to secondary sites.

While the invention has been described in detail and with reference to specific embodiments thereof, it will be apparent to one skilled in the art that various changes and modifications can be made therein without departing from the spirit and scope thereof.

Statement of Deposit

The hybridoma cell lines SNH3, NKH1, NKH2, NKH3 and NKH4 were deposited with the American Type Culture Collection, 12301 Parklawn Drive, Rockville, Md., on Jan. 5, 1989 and have Deposit Nos. HB 9941, 9942, 9943, 9944 and 9945, respectively. Hybridoma cells line SNH4 was deposited with the ATCC on Aug. 2, 1990 and has Deposit No. HB 10518.

The deposits were made in accordance with the terms of the Budapest Treaty on the International Recognition of the Deposit of Microorganisms for the Purpose of Patent Procedure.

All restrictions to access will be irrevocably removed upon grant of a United States patent on the instant application.

What is claimed is:

1. An in vitro method of treating blood for transplantation comprising exposing blood to:
   a therapeutically effective amount of an antibody produced by a method comprising:
   (1) immunizing a host with tumor cells expressing gangliosides;
   (2) boosting said host with a suspension comprising a mixture of tumor cell membrane and at least one purified lactonized tumor-associated ganglioside;
   (3) boosting said host with an immunogen comprising a lactone of a tumor associated ganglioside;
   (4) fusing immunized cells from said host with myeloma cells to form hybridoma cells;
   (5) selecting hybridoma cells that produce antibody that binds to said ganglioside of step (3) and does not react with hematopoietic progenitor cells;
   (6) culturing said selected hybridoma cells; and
   (7) recovering said antibody.

2. The method of claim 1 wherein said antibody is SNH3 having ATCC deposit number HB 9941.

3. The method of claim 1 wherein said antibody is SNH4 having ATCC deposit number HB 10518.

4. The method of claim 1 which further comprises exposing said blood exposed to said antibody to a therapeutically effective amount of complement.

* * * * *

UNITED STATES PATENT AND TRADEMARK OFFICE
CERTIFICATE OF CORRECTION

PATENT NO. : 5,418,129
DATED : May 23, 1995
INVENTOR(S) : Edward Nudelman, et al It is certified that error appears in the above-indentified patent and that said Letters Patent is hereby corrected as shown below:

Title page, item [57],
Abstract, line 14 after "antibody."
    insert -- The antibodies can be used to treat blood, binding to elements carrying tumor-associated gangliosides and fucogangliosides. --.

Col. 3, line 49 delete "Lex" and
    insert -- $Le^x$ -- .

Col. 7, line 31 delete "59" and
    insert -- 259 --.

Cols. 13 & 14 TABLE I, line 2 delete "NH3" and
    insert -- SNH3 --.

Cols. 13 & 14 TABLE I, line 4 delete "NH3" and
    insert -- SNH3--.

Col. 22, line 16 after "structure" and
    insert -- $Le^a$ --.

Signed and Sealed this

Twentieth Day of February, 1996

Attest:

BRUCE LEHMAN

*Attesting Officer*  *Commissioner of Patents and Trademarks*